| United States Patent [19] | [11] Patent Number: 5,034,276 |
| Zwiersch et al. | [45] Date of Patent: Jul. 23, 1991 |

[54] SIZING FOR GLASS FIBERS

[75] Inventors: Manfred Zwiersch; Edith Mäder, both of Dresden; Karl-Heinz Freitag, Ullersdorf; Rosemarie Plonka; Marianne Radatz, both of Oschatz; Heinz Momberg; Manfred Barth, both of Oschatz, all of German Democratic Rep.

[73] Assignee: Akademie der Wissenschaften der DDR, Berlin, German Democratic Rep.

[21] Appl. No.: 481,806

[22] Filed: Feb. 20, 1990

Related U.S. Application Data

[63] Continuation of Ser. No. 205,461, Jun. 10, 1988, abandoned.

[30] Foreign Application Priority Data

Jul. 1, 1987 [DD] German Democratic Rep. ..................................... 3044166

[51] Int. Cl.$^5$ .......................... B32B 25/20; C08K 5/54
[52] U.S. Cl. .................................... 428/391; 524/188; 524/306
[58] Field of Search ................ 524/128, 506; 106/287.11; 428/391

[56] References Cited

U.S. PATENT DOCUMENTS

| 4,271,229 | 6/1981 | Temple | 524/188 |
| 4,378,250 | 3/1983 | Treadway et al. | 106/287.11 |

Primary Examiner—Joseph L. Schofer
Assistant Examiner—Mark D. Sweet
Attorney, Agent, or Firm—Schweitzer Cornman & Gross

[57] ABSTRACT

The invention relates to a sizing for the treatment of glass fibers, which are incorporated into thermoplastic materials as reinforcement. The sizing contains a Schiff's base, preferably in concentrations of 0.05 to 2% by weight, based on the dry matter. Through the use of a sizing with this component, the tensile and impact strength properties of the glass fiber-reinforced thermoplastic materials are improved significantly.

Key Words

Sizing, glass fibers, roving preparation, glass fiber reinforcement, thermoplastic materials, tensile properties, tenacity properties.

5 Claims, No Drawings

SIZING FOR GLASS FIBERS

This is a continuing application of U.S. Ser. No. 205,461, filed on June 10, 1988, now abandoned.

FIELD OF THE INVENTION

The invention relates to a sizing for glass fibers, which are incorporated into thermoplastic materials to reinforce them. The sizing has a reactive silane as component. The composite properties are improved through the use of coated glass fibers in reinforced thermoplastic materials.

BACKGROUND OF THE INVENTION

The application of a sizing of usual composition on E glass fibers for reinforcing plastics is well known. As a rule, the glass fiber materials are prepared with a spinning sizing. It contains mainly suitable coupling agents for the manufacture of fiber glass, adhesive substances in aqueous dispersion for bundling the large number of individual fibers, as well as adjuvants for the processability of the yarns in subsequent steps (Loewenstein. K.L.: The manufacturing technology of continuous glass fibres. Elsevier Scientific Publishing Company, Amsterdam, London, N.Y., 1973. pages 191 to 233). On the basis of the plurality of sizing compositions described, it can be estimate that the sizing in its totality is constantly becoming more of an integral component of the composite and thus to an active carrier of the composite parameters.

For reinforcing polyolefins, polyamides and polyethylene terephthalates with glass fibers, the use of combinations of coupling agents, especially of aminosilanes, vinylsilanes and methacrylsilanes, is well known. The unambiguous assignment of special bonding agents to precise matrices is not described. The use is described in substance, but also as a special reaction product or as a bonding agent mixture. The known solutions generally achieve only a partial improvement in the mechanical properties of the glass fiber reinforced thermoplastic materials or it is a question of the reaction products of certain silanes, which are difficult to prepare or difficult to handle from the point of view of industrial safety. A clear improvement in all property parameters of the composites with justifiable modification expenditure has hardly been achieved so far.

Moreover, the synthesis and use of azidosilanes (diazo-, acidoformiate-, hexylsulfonylacidosilane), especially for reinforcing polyolefins, is known (German Offenlegungsschrift 2,528,382. German Offenlegungsschrift 2,528,398, British Patent 1,275,120). The use of azidosilanes is very disadvantageous from the point of view of industrial safety, since these silanes are very explosive. Silanes of the polyazamide type are used to increase the tensile strength of reinforced thermoplastic materials (German Offenlegungsschrift 2,802,242. German Offenlegungsschrift 2,802,243). Sizing compositions for thermoplastic materials are described, which bring about improved UV stability due to the use of an aliphatic urethane, ureido-functional silanes and aminosilane (German Offenlegungsschrift 3,101,457). To improve the adhesion of polyolefins to glass fibers, the additional incorporation of t-butyl hydroxyethyl peroxide is described in Belgian patent 89,238. The advantageous use of a sizing with silicon aminimide compounds for reinforcing plastics and elastomers is described in U.S. Pat. No. 3,946,131. Moreover, mercapto compounds are used, which are inhibited reversibly, for example, by reaction with isocyanates (U.S. Pat. No. 4,184,998). The synthesis of reactive silanes from mercapto- or aminosilanes and dicarboxylic acids is also described (U.S. Pat. No. 3,922,436). Furthermore, the reactions of amino , epoxy- or mercaptosilanes with diethylene glycol ethers is also described (European Patent 85,831). For the preparation of reinforced plastics, aziridins moreover are used as fiber matrix bonding agent (Japanese Patent 48 100 438). The use of carboxyamidotrialkoxysilanes as glass fiber adhesive substance is described in the Belgian Patent 824,644). Reinforced thermoplastic compositions can also be prepared by the use of 0.05 to 5.5% by weight of a metallocene of the general formula $(C_6H_5)_2MeX_2$ or a combination of a ferrocene derivative with an acryloxysilane (German Offenlegungsschrift 2,223,022). For the treatment of reinforcing glass fibers, a silane has also been described, which has 2 to 3 hydrolyzable groups on the silicon and an organic groups with a polyalkylene oxide structure (German Offenlegungsschrift 2,743,682). Bonding agents for reinforcing polymers are also known, which are based on an aminosilane with an azamide group and at least one secondary or tertiary amino group (European Patent 12 834). as well as on the reaction of an aminosilane with bis(maleic imide) in methylene chloride (British Patent 1,477,792) and also on the use of aminimide silane, prepared from epoxysilane with dialkylhydrazine (U.S. Pat. No. 3,949,140).

DESCRIPTION OF THE INVENTION

The object of the invention is to prepare sizings, which raise the level of composite parameters in glass fiber-reinforced thermoplastic materials.

The invention is based on the task of using suitable sizing compositions for the surface treatment of glass fibers. Pursuant to the invention this task is accomplished owing to the fact that the sizing contains a Schiff's base. This special reactive silane is prepared from a conventional aminosilane and a simple ketone, using a catalyst, which in itself is known. Without additional purification or further processing steps, it is used from the reaction solution in the sizing. It is advantageous that the sizing contains the Schiff's base in concentrations of 0.05 to 2% by weight, based on the dry matter. A preferred embodiment of the sizing contains 10 to 60% by weight polyolefin, 0 to 50% by weight polyurethane, up to 1% by weight vinylsilane and 0.05 to 2% by weight Schiff's base, based on the dry matter on the glass fibers. The drying of the sizing takes place at a temperature of at least 125° C.

Through this sizing, preferably during the manufacture of rovings, the tensile and tenacity properties of the glass fiber-reinforced thermoplastic materials are improved significantly.

The invention is explained in greater detail in the following.

CONTROL 1 a) Composition of the sizing, which is not of the invention.

| | |
|---|---|
| polyolefin dispersion of Example 1 | 5.0% by weight |
| polyurethane dispersion of Example 1 | 4.5% by weight |
| A-172 | 0.2% by weight |
| NB 1114 | 1.0% by weight |
| lubricant | 0.25% by weight | b) The sizing is prepared and the appropriate glass fibers are produced and dried as in Example 1.

An E glass fiber sized as above, has an impact strength of 45.7 and 38.7 kJ/m² obtained in the compound preparation with polyamide or chemically coupled polypropylene (in each case, 30% by weight of glass).

Tensile strengths of 115 and 64 MPa, respectively, are obtained (tested with 80×10× ∝ mm ISO bars). When glass fibers sized as in Example 1 are used, the impact strength values are increased to about 140% for polyamide and to about 145% for the chemically coupled polypropylene. The tensile strengths attain increases to 105% and 120% respectively by employing Example 1 of the present invention.

EXAMPLE 1 a) Preparation of the Schiff's Base

γ-Aminopropyltriethoxysilane (130 g, sold under the designation A-1100 by Union Carbide Corp.) in a round bottom flask is mixed slowly at room temperature with stirring with 100 g acetone. Subsequently. 0.1 g p-toluenesulfonic acid are added. After a short induction period, the reaction mixture warms up slowly to 25° to 27° C. To complete the reaction, stirring is continued for about 1 hour at 30° C.

A clear, slightly yellow solution results, which can be added without further working up in the appropriate amount to the sizing formulation.

b) Composition of the sizing

| | |
|---|---|
| polyolefin dispersion (prepared from a 30% by weight partially saponified, oxidized, polyethylene wax with a molecular weight of between 1,500 and 2,000 and 70% deionized water; "Marvelan PED", manufacturer: Fettchemie Karl-Marx-Stadt) | 5.0% by weight |
| polyurethane dispersion ("Xionel 9851"), manufacturer: SAVID/Italy | 4.5% by weight |
| lubricant (for example, a fatty acid ester of a polyglycol | 0.25% by weight |
| vinyl-tris-(2-methoxy)silane (A-172, union carbide) | 0.2% by weight |
| Schiff's base | 2.0% by weight |
| deionized water | to 100.0% by weight | c) Preparation of the Sizing

About one tenth of the total amount of water is added to a mixing vessel and adjusted to a pH of 4.5 with dilute acetic acid. The appropriate amount of Schiff's base is added slowly. After 2 minutes, the pH of the solution is adjusted with half concentrated acetic once again to a value of 4 to 4.5. After that the vinylsilane is added.

Stirring is continued for 20 to 30 minutes to complete the hydrolysis. The rest of the water is added to a different mixing vessel, to which the polyolefin dispersion, the polyurethane dispersion and the lubricant are then added one after the other.

In the last step of the procedure, the coupling agent and the binder mixture are added.

The mixture as a whole is adjusted to a pH of 4.5 with acetic acid.

d) Preparation and Drying of the Sized Glass Fibers

The glass fibers are produced in the known manner by drawing streams of molten glass, which are flowing through the openings of a spinner et. These streams of glass are drawn out thin, the drawing out being accomplished by winding the filaments after they have been combined into a spinning thread) on a rotating tube. Before being combined to a spinning thread, the fibers are coated in a known manner with the sizing by means of a sizing device that is supplied continuously with sizing. The spin moist spools are dried in a hot-air oven at 125° to 140° C.

The roving of sized glass fibers (2400 tex) has few slubs, shows good dispersion in the elementary fibers and is not discolored.

EXAMPLE 2 a) The Schiff's base is prepared as in Example 1 b) Composition of the Sizing

| | |
|---|---|
| polyolefin dispersion of Example 1 | 5.0% by weight |
| polyurethane dispersion of Example 1 | 4.5% by weight |
| lubricant | 0.25% by weight |
| vinyl-tris-(2-methoxyethoxy)silane | 0.1% by weight |
| Schiff's base of Example 1 | 2.0% by weight |
| chromium complex (for example, VOLAN A, manufactured by DU PONT) | 0.5% by weight |
| deionized water | to 100.0% by weight | c) Preparation of the Sizing

One tenth of the total amount of water is added to a mixing vessel and adjusted to a pH of 4.5 with dilute acetic acid. The appropriate amount of Schiff's base is added slowly. Subsequently, the chromium complex is added slowly with vigorous stirring. After 2 minutes, the pH of the solution is adjusted with half concentrated acetic to a value of 4 to 4.5. After that the vinylsilane is added. To complete the hydrolysis, stirring is continued for about 20 to 30 minutes. The addition of the further sizing components and the combining of the part solutions is accomplished as in Example 1.

d) The preparation and drying of the sized glass fibers is explained in Example 1.

The roving from the sized glass fibers (2,400 tex) has few slubs, shows good dispersion of the elementary fibers and has a soft handle. It is not discolored.

When glass fibers, sized as in Example 2, are used, values are obtained for the impact strength, which are increased to about 140% in the case of polyamide and to about 160% in the case of chemically coupled polypropylene. The tensile strengths attain increases of 108% and 120% respectively.

We claim:

1. A process for treating a reinforcing glass fiber prior to it being embedded for reinforcing, which comprises applying a composition to the surface of said glass fiber, said composition comprising a solution of a Schiff's base which also functions as a reactive silane, said solution being prepared from a conventional aminosilane and a simple ketone by the use of a catalyst.

2. The process of claim 1, wherein said composition comprises from about 0.05% to about 2% by weight solids, of said Schiff's base.

3. The process of claim 1, wherein said composition comprises an aqueous solution of Schiff's base.

4. The process of claim 1, wherein said composition comprises from about 10% to about 60% be weight based on the solids in said composition of a polyolefin, about 1% to about 50% by weight of a polyurethane, from 0% to about 1% by weight of a vinylsilane, and from about 0.05% to about 2% by weight of said Schiff's base.

5. The process of claim 1, further comprises drying said composition on said glass fiber, at a temperature of at least 125° C.

* * * * *